United States Patent

Simon

[11] Patent Number: 5,627,175
[45] Date of Patent: May 6, 1997

[54] AZOXYCYANOBENZENE COMPOUNDS

[75] Inventor: Werner E. J. Simon, Jungenheim, Germany

[73] Assignee: ShellInternationale Research Maatschappij B.V., The Hague, Netherlands

[21] Appl. No.: 446,716

[22] PCT Filed: Nov. 29, 1993

[86] PCT No.: PCT/EP93/03370

§ 371 Date: Jul. 24, 1995

§ 102(e) Date: Jul. 24, 1995

[87] PCT Pub. No.: WO94/12470

PCT Pub. Date: Jun. 9, 1994

[30] Foreign Application Priority Data

Dec. 2, 1992 [EP] European Pat. Off. .............. 92120580

[51] Int. Cl.$^6$ .................... C07C 291/08; A01N 51/00
[52] U.S. Cl. ..................... 514/150; 514/149; 534/556; 534/566; 534/558; 534/572
[58] Field of Search ................... 534/556, 558; 514/149, 150

[56] References Cited

U.S. PATENT DOCUMENTS

| Re. 24,960 | 4/1961 | Urbschat et al. ................... 534/558 X |
| 1,909,851 | 5/1933 | Zitscher et al. .................... 534/558 |
| 3,819,609 | 6/1974 | Puklics et al. ...................... 534/556 |
| 4,550,121 | 10/1985 | Pilgrim et al. ....................... 514/469 |
| 4,558,040 | 12/1985 | Pilgrim et al. ....................... 514/150 |
| 4,883,137 | 11/1989 | Gilkerson et al. ................... 514/224.2 |
| 5,089,486 | 2/1992 | Wood et al. ........................ 534/566 X |
| 5,298,606 | 3/1994 | Wood et al. ........................ 534/556 |
| 5,439,897 | 8/1995 | Simon ..................... 514/149 |
| 5,475,093 | 12/1995 | Simon ..................... 534/572 |

FOREIGN PATENT DOCUMENTS

| 0245902 | 11/1987 | European Pat. Off. ............... 534/556 |
| 0411716 | 2/1991 | European Pat. Off. ............... 534/556 |
| 0411720 | 2/1991 | European Pat. Off. ............... 534/556 |
| 52-071444 | 6/1977 | Japan ..................... 514/149 |
| 94-012470 | 6/1994 | WIPO ..................... 534/566 |

OTHER PUBLICATIONS

Mortarini et al., "Synthesis, Antibacterial and Antifungal Activity of Phenylazoxycyanide Derivatives", *European Journal of Medicinal Chemistry*, vol. 12, No. 1, 1977, pp. 59–62.

*Primary Examiner*—Floyd D. Higel
*Attorney, Agent, or Firm*—Charles F. Costello, Jr.

[57] ABSTRACT

The invention is directed to azoxycyanobenzene derivatives of the formula:

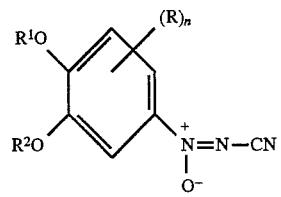

wherein n is 0–3; each R represents halogen, nitro, cyano, alkyl, haloalkyl, alkoxy, or haloalkoxy; and each $R^1$ and $R^2$ represents an optionally substituted alkyl, alkenyl, alkynyl, cycloalkyl, or aralkyl group. The compounds may be used as fungicides.

13 Claims, No Drawings

AZOXYCYANOBENZENE COMPOUNDS

This application is a 371 08 PCT/EP93/03370 filed Nov. 29, 1993.

This invention relates to certain azoxycyanobenzene derivatives, processes for their preparation, compositions containing such compounds and their use as fungicides.

Eur. J. Med. Chem.-Chimica Therapeutica, 12(1), (1977), pp. 59–62 discloses, inter alia, 2-methoxy-1-azoxycyanobenzene, 3-methoxy-1-azoxycyanobenzene and 4-methoxy-1-azoxycyanobenzene which are shown to have antibacterial and antifungal properties against bacteria and fungi of interest in the medical field. However, there is no indication that these compounds have any activity against phytopathogenic fungi of agronomic importance.

It has now been discovered that certain azoxycyanobenzene derivatives exhibit good activity against certain phytopathogenic fungi.

According to the present invention there is therefore provided a compound of general formula

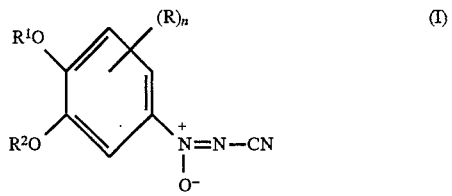

in which n is 0, 1, 2 or 3; each R independently represents a halogen atom, nitro, cyano, alkyl, haloalkyl, alkoxy or haloalkoxy group; and each of $R^1$ and $R^2$ independently represents an optionally substituted alkyl, alkenyl, alkynyl, cycloalkyl or aralkyl group.

When the compounds of this invention contain an alkyl or alkenyl substitutent group, this may be linear or branched and may contain up to 12, preferably up to 6 and especially up to 4, carbon atoms. Cycloalkyl groups may contain 3 to 8, preferably 3 to 6, carbon atoms. An aralkyl group comprises an alkyl group, as defined above, substituted by an aryl group. The aryl group may be any aromatic hydrocarbon group, especially a phenyl or naphthyl group. A particularly preferred example of an aralkyl group is a benzyl group.

When any of the foregoing substituents are designated as being optionally substituted, the substituent groups which are optionally present may be any one or more of those customarily employed in the development of pesticidal compounds, and/or the modification of such compounds to influence their structure/activity, persistence, penetration or other property. Specific examples of such substituents include, for example, halogen atoms, nitro, cyano, hydroxyl, alkyl, haloalkyl, alkoxy, haloalkoxy, phenoxy, amino, alkylamino, dialkylamino, formyl, alkoxycarbonyl, morpholinocarbonyl, carboxyl, alkanoyl, alkylthio, alkylsulphinyl, alkylsulphonyl, carbamoyl, alkylcarbamoyl and alkylamido groups. When any of the foregoing substituents represents or contains an alkyl substituent group, this may be linear or branched and may contain up to 12, preferably up to 6, and especially up to 4, carbon atoms. Typically, 0–3 substituents may be present, most commonly 0 or 1.

Preferably, each R independently represents a halogen atom, nitro, cyano, $C_{1-6}$ alkyl, $C_{1-6}$ haloalkyl, $C_{1-6}$ alkoxy or $C_{1-6}$ haloalkoxy group.

More preferably, each R independently represents a halogen (especially fluorine or chlorine) atom, $C_{1-4}$ alkyl (especially methyl) or $C_{1-4}$ haloalkyl (especially trifluoromethyl) group.

It is preferred that n is 0 or 1 and especially preferred that n is 0.

It is also preferred that each of $R^1$ and $R^2$ independently represents a $C_{1-8}$ alkyl, $C_{2-6}$ alkenyl, $C_{2-6}$ alkynyl, $C_{3-8}$ cycloalkyl or benzyl group, each group being optionally substituted by one or more substituents selected from halogen atoms, nitro, cyano, hydroxyl, $C_{1-4}$ alkyl, $C_{1-4}$ haloalkyl, $C_{1-4}$ alkoxy, $C_{1-4}$ haloalkoxy, phenoxy, amino, $C_{1-4}$ alkylamino, di-$C_{1-4}$ alkylamino, $C_{1-4}$ alkoxycarbonyl, morpholinocarbonyl, and $C_{1-4}$ alkylcarbamoyl groups.

More preferably, each of $R^1$ and $R^2$ independently represents a $C_{1-6}$ alkyl, $C_{2-4}$ alkenyl, $C_{2-4}$ alkynyl, $C_{3-6}$ cycloalkyl or benzyl group, each group being optionally substituted by one or more substituents selected from halogen atoms, hydroxy, phenoxy, $C_{1-4}$ alkyl, $C_{1-4}$ alkoxycarbonyl, methylcarbamoyl and morpholinocarbonyl groups.

A particularly preferred sub-group of compounds of formula I is that in which n is 0 and each of $R^1$ and $R^2$ independently represents a methyl, ethyl, propyl, hexyl, hydroxyethyl, phenoxyethyl, trifluoromethyl, dibromopropyl, ethoxycarbonylmethyl, diethoxycarbonylmethyl, 2-(ethoxycarbonyl) pentyl, propenyl, propynyl, cyclopentyl, cyclohexyl, methylcarbamoylmethyl, morpholinocarbonymethyl, benzyl, p-bromobenzyl or tert-butylbenzyl group.

It should also be noted that compound of general formula I could be in any of the following isoelectronic forms:

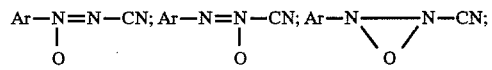

where Ar represents

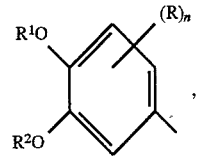

and the scope of the present invention covers all such forms.

The present invention also provides a process for the preparation of a compound of formula I as defined above which comprises treating a compound of general formula

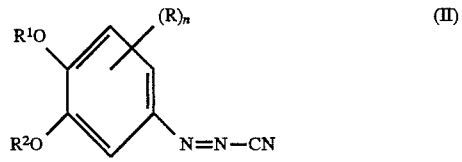

in which n, R, $R^1$ and $R^2$ are as defined above, with a mixture comprising hydrogen peroxide and methanoic acid and/or with peroxymethanoic acid.

Where a mixture of hydrogen peroxide and methanoic acid is used, the concentration of the hydrogen peroxide is suitably less than about 75 wt %, preferably less than about 50 wt % and, more preferably, less than 40 wt %. In a preferred embodiment the concentration of hydrogen peroxide is about 30 wt %.

The process is preferably carried out at or above, more preferably, above, ambient temperature. The process may be carried out at a temperature in the range from 25° C. to 75° C., preferably in the range from 30° C. to 50° C.

Preferably, the compound of general formula II is mixed with methanoic acid and hydrogen peroxide at ambient temperature. The mixture is preferably then heated, suitably at about 60° C., for a number of hours. The mixture may then be cooled, for instance, in an ice bath. The desired product may then be isolated by standard techniques.

A general process for the preparation of compounds of formula II is provided by R. J. W. LeFevre and H. Vine, J. Chem. Soc., (1938), 431.

The present invention further provides an alternative process for the preparation of a compound of formula I as defined above which comprises reacting a compound of general formula

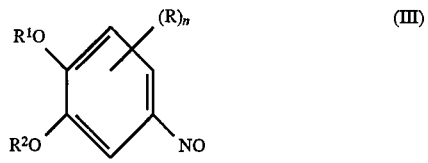

in which n, R, $R^1$ and $R^2$ are as defined above, with cyanamide.

Suitably, the reaction takes place in the presence of an organic solvent, preferably a halogenated hydrocarbon, for example, dichloromethane, and in the presence of iodobenzene diacetate or dibromoisocyanuric acid. The reaction is preferably effected at a temperature in the range from –20° C. to 50° C.

A compound of formula III may be prepared as follows, where Ar is as defined above:

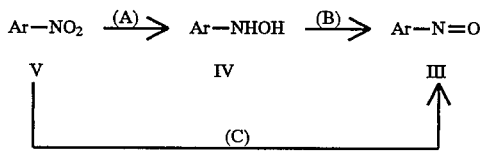

Reaction A may, for example, be effected by reaction of the nitro compound with hydrazine hydrate, in the presence of a hydrogen transfer catalyst, for example rhodium on carbon, suitably in the presence of an inert polar organic solvent, for example, tetrahydrofuran, preferably with cooling; or be effected using water, stannous chloride as reducing agent, an inert, polar organic solvent, for example tetrahydrofuran, under an inert atmosphere, for example nitrogen, in the presence of sodium acetate, suitably at ambient temperature.

Reaction B may suitably be effected by treatment of the hydroxylamine derivative with an oxidising agent, for example an $Fe^{3+}$ compound, suitably ferric chloride. The reaction may be effected in a mixed water/polar organic solvent, preferably with cooling.

Reaction C may be effected by irradiating the nitro compound, which is preferably dissolved in an inert organic solvent, for example benzene. The irradiation may be effected using a medium pressure mercury lamp.

Other methods suitable for preparing compounds of formula I, and further descriptions of the methods described herein, may be found in The Journal of Antibiotics, Jan. 1975, p.87–90 and June 1986, p.864–868; in Eur.J.Med. Chem.-Chim. Ther., 1982, 17, No. 5, p.482–484, and 1980, 15, No.5, p.475–478, and 1977, 12, No.1, p.59–62; in J.Chem. Soc.,Chem. Commun., 1984, p.323–324; in Chem. Ind. (Milan), 1977, 59(5), p.385; in Gazetta Chimica Italiana, 106, 1976, p.1107–1110; in Tetrahedron Letters, No. 38, 1974, p. 3431–3432; and in U.S. Pat. Nos. 4,558,040 and 4,550,121.

The compounds of general formula I have been found to have fungicidal activity. Accordingly, the invention further provides a fungicidal composition which comprises a carrier and, as active ingredient, a compound of formula I as defined above. A method of making such a composition is also provided which comprises bringing a compound of formula I as defined above into association with at least one carrier. Such a composition may contain a single compound or a mixture of several compounds of the present invention. It is also envisaged that different isomers or mixtures of isomers may have different levels or spectra of activity and thus compositions may comprise individual isomers or mixtures of isomers.

A composition according to the invention preferably contains from 0.5 to 95% by weight of active ingredient, A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating fungicidal compositions may be used.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes, for example beeswax, paraffin wax, and chlorinated mineral waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example, kerosine and light mineral oils; chlorinated hydrocarbons, for example carbon tetrachloride, perchloroethylene and trichloroethane. Mixtures of different liquids are often suitable.

Fungicidal compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitol, sucrose or pentaervthritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3–10% w of a dispersing agent and, where necessary, 0–10% w of stabiliser(s) and/or other additives such as penetrants or stickers. Dusts are usually formulated as a dust concentrate having a similar composition to that of a wettable powder but without a dispersant, and may be diluted in the field with further solid carrier to give a composition usually containing ½–10% w of active ingredient. Granules are usually prepared to have a size between 10 and 100 BS mesh (1.676–0.152 mm), and may be manufactured by agglomeration or impregnation techniques. Generally, granules will contain ½–75% w active ingredient and 0–10% w of additives such as stabilisers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 1–50% w/v active ingredient, 2–20% w/v emulsifiers and 0–20% w/v of other additives such as stabilisers, penetrants and corrosion inhibitors. Suspension concentrates are usually compounded so as to obtain a stable, non-sedimenting flowable product and usually contain 10–75% w active ingredient, 0.5–15% w of dispersing agents, 0.1–10% w of suspending agents such as protective colloids and thixotropic agents, 0–10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as anti-freeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise' like consistency.

The composition of the invention may also contain other ingredients, for example other compounds possessing herbicidal, insecticidal or fungicidal properties.

Of particular interest in enhancing the duration of the protective activity of the compounds of this invention is the use of a carrier which will provide a slow release of the fungicidal compounds into the environment of the plant which is to be protected. Such slow-release formulations could, for example, be inserted in the soil adjacent to the roots of a vine plant, or could include an adhesive component enabling them to be applied directly to the stem of a vine plant.

The invention still further provides the use as a fungicide of a compound of the general formula I as defined above or a composition as defined above, and a method for combating fungus at a locus, which comprises treating the locus, which may be for example plants subject to or subjected to fungal attack, seeds of such plants or the medium in which such plants are growing or are to be grown, with such a compound or composition. A locus as described above may suitably be treated with a compound I at an application rate in the range 0.05 to 4 kg/ha, preferably 0.1 to 1 kg/ha.

The present invention is of wide applicability in the protection of crop plants against fungal attack. Typical crops which may be protected include vines, grain crops such as wheat and barley, apples and tomatoes. The duration of protection is normally dependent on the individual compound selected, and also a variety of external factors, such as climate, whose impact is normally mitigated by the use of a suitable formulation.

The invention is further illustrated by the following examples.

EXAMPLE 1

Preparation of 3,4-dimethoxy-1-azoxycyanobenzene (n=0; $R^1=R^2=CH_3$)

(a) Preparation of 3,4-dimethoxy-1-azocyanobenzene 3,4-Dimethoxyaniline (3.8 g, 25 mmol) was dissolved in methanol (20 ml). Hydrochloric acid (20 ml, 20 % w/w) was added and the solution was diazotised by the addition of sodium nitrite (3.8 g, 55 mmol). Ethyl ethanoate (70 ml) was added and the reaction mixture was cooled to about −10° C. After the addition of sodium cyanide (2.5 g, 51 mmol) dissolved in water (5 ml), the reaction mixture was stirred for 30 minutes. The organic layer was separated, dried over sodium sulphate and evaporated to dryness. The resulting brown-orange solid was recrystallised from petroleum ether/dichloromethane to give 2.6 g (55% yield) 3,4-dimethoxy-1-azocyanobenzene, m.p. 173°–178° C.

(b) Preparation of 3,4-dimethoxy-1-azoxycyanobenzene 3,4-Dimethoxy-1-azocyanobenzene (2.0 g, 10 mmol) obtained in (a) was suspended in a mixture of methanoic acid (30 ml) and hydrogen peroxide (10 ml, 30% w/w). The mixture was heated to 60° C. for 24 hours and then cooled in an ice bath. The resulting orange crystals were collected and washed with water to give 1.56 g (72% yield) 3,4-dimethoxy-1-azoxycyanobenzene, mp. 157° C., m/e ($M^+$): 207.

Analysis: Calc. % C 52.2 H 4.4 N 20.2 Found % C 52.5 H 4.4 N 20.0

EXAMPLE 2

Preparation of 3-n-hexyloxy-4-methoxy-1-azoxycyanobenzene (n=0; $R^1=CH^3$; $R^2={}^nC_4H_9$)

3-n-Hexyloxy-4-methoxy-1-nitrosobenzene (2.3 g, 11 mmol) and cyanamide (0.69 g, 16 mmol) were dissolved in dichloromethane (120 ml). Under nitrogen, a solution of iodobenzene diacetate (3.49 g, 11 mmol) in dichloromethane was added drop by drop at 0° C. The mixture was stirred overnight at ambient temperature, filtered and evaporated to dryness. Column chromatography on silica using 8:1 petroleum ether:ethyl ethanoate as eluant yielded 1.4 g (52% yield) 3-n-hexyloxy-4-methoxy-1-azoxycyanobenzene as a yellow powder, m.p. 80°–82° C., m/e ($M^+$): 277.

Analysis: Calc. % C 60.6 H 6.9 N 15.2 Found % C 60.3 H 6.7 N 15.3

EXAMPLE 3

Preparation of 3-methoxy-4-ethoxycarbonylmethoxy-1-azoxycyanobenzene
(n=0; $R^1=-CH_2CO-OCH_2CH_3$; $R^2=CH_3$)

3-Methoxy-4-ethoxycarbonylmethoxy-1-nitrosobenzene (2.1 g, 11.6 mmol) was dissolved in dichloromethane (50 ml). Cyanamide (0.38 g, 9.0 mmol) and dibromoisocyanuric acid (1,3-dibromo-1,3,5-triazin-2,4,6(1H,3H,5H)-trione; 2.5 g, 8.7 mmol) were added under nitrogen at 0° C. The mixture was stirred for 4 hours at ambient temperature and the resulting yellow suspension filtered and evaporated to dryness. Column chromatography on silica using 4:1 petroleum ether:ethyl ethanoate as eluant yielded 1.1 g (45% yield) 3-methoxy-4-ethoxycarbonylmethoxy-1-azoxycyanobenzene as a yellow solid, m.p. 115°–117° C., m/e (M$^+$):267.

Analysis: Calc. % C 51.6 H 4.7 N 15.0 Found % C 51.3 H 4.9 N 14.8

EXAMPLES 4 TO 22

By processes similar to those described in Examples 1 to 3 above, further compounds according to the invention were prepared as detailed in Table I below. In this table the compounds are identified by reference to formula I. Melting point, mass spectroscopy (m/e) and C,H,N analysis data for the compounds of Examples 4 to 22 are given in Table IA below.

TABLE I (N.B. In all the following examples n = 0)

| Example No. | R$^1$ | R$^2$ |
|---|---|---|
| 4 | —CH$_3$ | —(CH$_2$)$_3$CH$_3$ |
| 5 | —CH$_3$ | —CH$_2$CH$_3$ |
| 6 | —CH$_3$ | —CH(CH$_3$)$_2$ |
| 7 | —CH$_3$ | —CH$_2$—CO—OCH$_2$CH |
| 8 | —CH$_3$ | cyclopentyl |
| 9 | —CH$_3$ | —CH$_2$C CH |
| 10 | —CH$_3$ | —CH$_2$CH=CH$_2$ |
| 11 | —CH$_3$ | benzyl |
| 12 | —CH$_2$CH$_3$ | —CH$_2$CH$_3$ |
| 13 | —CH$_2$CH$_3$CH$_3$ | —CH$_2$CH$_2$CH$_3$ |
| 14 | —CH$_2$C CH | —CH$_2$C CH |
| 15 | —CH$_2$CH$_3$ | —CH$_3$ |
| 16 | —CH$_2$CHBrCH$_2$Br | —CH$_3$ |
| 17 | —CH$_2$C CH | —CH$_3$ |
| 18 | benzyl | —CH$_3$ |
| 19 | —CH(CH$_3$)2 | —CH$_3$ |
| 20 | —(CH$_2$)$_5$CH$_3$ | —CH$_3$ |
| 21 | cyclopentyl | —CH$_3$ |
| 22 | 4-(tert-C$_4$H$_9$)benzyl | —CH$_3$ |
| 23 | —CH$_2$CH$_2$CH$_3$ | —CH$_2$CH$_2$CH$_3$ |
| 24 | —CH$_2$CH$_2$OH | CH$_3$ |
| 25 | —CH$_2$CO-morpholino | CH$_3$ |
| 26 | —CH(COOC$_2$H$_5$)$_2$ | CH$_3$ |
| 27 | —CH$_2$CH(COOC$_2$H$_5$)CH$_2$CH$_2$CH$_3$ | CH$_3$ |
| 28 | -Cyclohexyl | CH$_3$ |
| 29 | —CH$_2$CH$_2$O Phenyl | CH$_3$ |
| 30 | —CH$_2$-p-BrPhenyl | CH$_3$ |
| 31 | —CH$_2$CONHCH$_3$ | CH$_3$ |

TABLE IA

| | | | Elemental Analysis (%) | | | | | |
|---|---|---|---|---|---|---|---|---|
| | | | C | | H | | N | |
| Ex. No. | m.p. (°C.) | m/e M$^+$) | Calc. | Found | Calc. | Found | Calc. | Found |
| 4 | 84 | 249 | 57.8 | 57.9 | 6.1 | 6.3 | 16.9 | 17.0 |
| 5 | 150 | 221 | 54.3 | 54.0 | 5.0 | 5.2 | 19.0 | 18.9 |
| 6 | 98–100 | 235 | 56.1 | 54.7 | 5.6 | 5.6 | 17.8 | 17.4 |
| 7 | 118 | 267 | 51.6 | 51.8 | 4.7 | 4.9 | 15.0 | 14.9 |
| 8 | 76–78 | 261 | | | | | | |
| 9 | 142 | 231 | | | | | | |
| 10 | 93 | 233 | 56.7 | 56.9 | 4.8 | 5.0 | 18.0 | 17.8 |
| 11 | 123–125 | 283 | 63.6 | 62.9 | 4.6 | 4.8 | 14.8 | 14.2 |
| 12 | | 235 | | | | | | |
| 13 | | 259 | | | | | | |
| 14 | 136 | 251 | | | | | | |
| 15 | | 221 | 54.3 | 53.3 | 5.0 | 5.2 | 19.0 | 18.5 |
| 16 | 83 | 387/389/391 79/81$_{Br}$ | 33.6 | 34.1 | 2.8 | 3.0 | 10.7 | 10.7 |
| 17 | 118 | 231 | | | | | | |
| 18 | 141–145 | 283 | 63.6 | 62.7 | 4.6 | 4.6 | 14.8 | 14.4 |
| 19 | 117 | 235 | | | | | | |
| 20 | 91 | 277 | | | | | | |

TABLE IA-continued

| | | | Elemental Analysis (%) | | | | | |
|---|---|---|---|---|---|---|---|---|
| | | | C | | H | | N | |
| Ex. No. | m.p. (°C.) | m/e M⁺) | Calc. | Found | Calc. | Found | Calc. | Found |
| 21 | 135–137 | 261 | 59.7 | 59.2 | 5.7 | 5.7 | 16.0 | 15.8 |
| 22 | 120–122 | 339 | | | | | | |
| 23 | 70 | | | | | | | |
| 24 | 126 | | | | | | | |
| 25 | 190 | | | | | | | |
| 26 | 113 | | | | | | | |
| 27 | 110 | | | | | | | |
| 28 | 99 | | | | | | | |
| 29 | 172 | | | | | | | |
| 30 | 160 | | | | | | | |
| 31 | 179–183 | | | | | | | |

EXAMPLE 32

The fungicidal activity of compounds of the invention was investigated by means of the following tests.

(a) Antisporulant activity against vine downy mildew (*Plasmopara viticola*; PVA)

The test is a direct antisporulant one using a foliar spray. The lower surface of leaves of vine plants (cv. Cabernet Sauvignon), approximately 8 cm high, are inoculated with an aqueous suspension containing $5 \times 10^4$ zoosporangia/ml. The inoculated plants are kept for 24 hours at 21° C. in a high humidity cabinet, then for 24 hours in a glasshouse at 20° C. and 40% relative humidity. Infected leaves are sprayed on their lower surfaces with a solution of the test compound in 1:1 water/acetone containing 0.04% "TWEEN 20" (Trade Mark; a polyoxyethylene sorbitan ester surfactant). Plants are sprayed using a track sprayer equipped with 2 air-atomising nozzles. The concentration of the compound is 600 ppm and the spray volume is 750 l/ha. After drying, the plants are returned to the glasshouse at 20° C. and 40% relative humidity for 96 hours and are then transferred to the high humidity cabinet for 24 hours to induce sporulation. Assessment is based on the percentage of the leaf area covered by sporulation compared with that on control leaves.

(b) Direct protectant activity against tomato late blight (*Phytophthora infestans*; PIP)

The test is a direct protectant one using a foliar spray. Tomato plants with two expanded leaves (cv. First in the Field) are sprayed with the test compound at a dosage of 600 ppm as described under (a). After drying, the plants are kept for 24 hours in a glasshouse at 20° C. and 40% relative humidity. The upper surfaces of the leaves are then inoculated with an aqueous suspension containing $2 \times 10^5$ zoosporangia/mi. The inoculated plants are kept for 24 hours at 18° C. in a high humidity cabinet and then for 5 days in a growth chamber at 15° C. and 80% relative humidity with 14 hours light/day. The assessment is based on the percentage of diseased leaf area compared with that on control leaves.

(c) Activity against tomato early blight (*Alternaria solani*; AS)

The test is a direct prophylactic one using a foliar spray. Tomato seedlings (cv Outdoor Girl), at the stage at which the second leaf is expanded, are sprayed with the test compound at a dosage of 600 ppm as described under (a). After drying, the plants are kept for 24 hours in a glasshouse at 20° C. and 40% relative humidity followed by inoculation of the leaf upper surfaces with an aqueous suspension of *A. solani* conidia containing $1 \times 10^4$ conidia/ml. After 4 days in a high humidity cabinet at 21° C., disease is assessed based on the percentage of leaf surface area covered by lesions when compared with control plants.

(d) Direct protectant activity against broad bean grey mould (*Botrytis cinerea*; BCB)

The test is a direct protectant one using a foliar spray. Broad bean plants (cv The Sutton) with two leaf pairs are sprayed with the test compound at a dosage of 600 ppm as described under (a). After drying, the plants are kept for 24 hours in a glasshouse at 20° C. and 40% relative humidity. The upper surface of the leaves are then inoculated with an aqueous suspension containing $1 \times 10^6$ conidia/ml. Plants are kept for 4 days at 22° C. in a high humidity cabinet. The assessment is based on the percentage of diseased leaf area compared with that on control leaves.

(e) Activity against wheat leafspot (*Leptosphaeria nodorum*; LN.)

The test is a direct therapeutic one using a foliar spray. Wheat seedlings (cv Norman), at the single leaf stage, are inoculated with an aqueous suspension containing $1.5 \times 10^6$ conidia/ml. The inoculated plants are kept for 24 hours at 20° C. in a high humidity cabinet followed by spraying with the test compound at a dosage of 600 ppm as described under (a). After drying, the plants are kept for 6–8 days in a glasshouse at 22° C. and 70% relative humidity. Assessment is based on the density of lesions per leaf compared with that on leaves of control plants.

(f) Activity against wheat eyespot in-vitro (*Pseudocercosporella herpotrichoides*; PHI)

This test measures the in vitro activity of compounds against the fungus causing wheat eyespot. The test compound is dissolved or suspended in acetone and is added into 4 ml aliquots of half strength Potato Dextrose Broth dispensed in 25-compartment petri dishes to give a final concentration of 30 ppm test compound and 0.825% acetone. The fungal inoculum consists of mycelial fragments of *P. herpotrichoides* grown in half strength Potato Dextrose Broth in shaken flasks and added to the broth to provide $5 \times 10^4$ mycelial fragments/ml broth. Petri dishes are incubated at 20° C. for 10 days until the assessment of mycelial growth.

(g) Activity against Rhizoctonia in-vitro (*Rhizoctonia solani*: RSI)

The test measures the in-vitro activity of compounds against *Rhizoctonia solani* that causes stem and root rots. The test compound is dissolved or suspended in acetone and added into 4 ml aliquots of half strength Potato Dextrose Broth dispensed in 25-compartment petri dishes to give a final concentration of 30 ppm compound and 0.825% acetone. The fungal inoculum consists of mycelial fragments of *R. solani* grown in half strength Potato Dextrose Broth in shaken culture flasks and added to the broth to provide $5 \times 10^4$ fragments/ml broth. Petri dishes are incubated at 20° C. for 10 days until the assessment of mycelial growth.

(h) Activity against apple scab in-vitro (*Venturia inaequalis*; VII)

This test measures the in-vitro activity of compounds against Venturia inaequalis that causes apple scab. The test compound is dissolved or suspended in acetone and added into 4 ml aliquots of half strength Potato Dextrose Broth dispensed in 25-compartment petri dishes to give a final concentration of 30 ppm compound and 0.825% acetone. The fungal inoculum consists of mycelial fragments and spores of *V. inaequalis* grown on malt agar and added to the broth to provide $5 \times 10^4$ propagules/ml broth. Petri dishes are incubated at 20° C. for 10 days until the assessment of mycelial growth.

The extent of disease control in all the above tests is expressed as a rating compared with either an untreated control or a diluent-sprayed-control, according to the criteria:

0=less than 50% disease control

1=50–80% disease control

2=greater than 80% disease control

The results of these tests are set out in Table II below:

TABLE II

| Example No. | Fungicidal Activity | | | | | | |
|---|---|---|---|---|---|---|---|
| | PVA | PIP | AS | BCB | LN | PHI | RSI | VII |
| 1 | | 2 | 2 | 2 | 1 | 2 | | 2 |
| 2 | 1 | | | | | | 1 | |
| 3 | | | 2 | 2 | 1 | 2 | 2 | 2 |
| 4 | | | 2 | 2 | 1 | 1 | 2 | |
| 5 | 2 | 2 | 1 | 2 | | 1 | 2 | |
| 6 | | | 1 | 2 | 1 | 1 | 2 | |
| 7 | | | 2 | 2 | | | 2 | |
| 8 | 2 | 2 | | | 1 | 2 | 2 | |
| 9 | | 2 | 2 | | 1 | 1 | 1 | |
| 10 | | 2 | 2 | 2 | 1 | | 1 | |
| 11 | | 1 | | | | 1 | 2 | |
| 12 | | 2 | 2 | 2 | 1 | | 2 | |
| 13 | | | 2 | | | 1 | | 1 |
| 14 | | 1 | 2 | | | 2 | 1 | 1 |
| 15 | 2 | 2 | 2 | 2 | 2 | 2 | 2 | 2 |
| 16 | | 2 | | 1 | | | 1 | 2 |
| 17 | 2 | 2 | | | | 2* | 2* | 2* |
| 18 | | | 2 | | | 1* | | |
| 19 | | 2 | 2 | 1 | | 2* | 1* | 2* |
| 20 | | | | 1 | | 2* | | 1* |
| 21 | | | | | | 2* | | 2* |
| 22 | | | | | | 1* | | |

*signifies concentration of test compound = 10 ppm

I claim:

1. A compound of formula

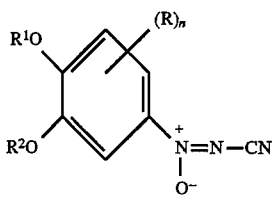

in which n is 0, 1, 2 or 3; each R independently represents a halogen atom, nitro, cyano, alkyl, haloalkyl, alkoxy or haloalkoxy group; and each of $R^1$ and $R^2$ independently represents a $C_{1-8}$ alkyl, $C_{2-6}$ alkenyl, $C_{2-6}$ alkynyl, $C_{3-8}$ cycloalkyl or benzyl group unsubstituted or substituted by one or more substituents selected from halogen atoms, nitro, cyano, hydroxyl, $C_{1-4}$ alkyl, $C_{1-4}$ haloalkyl, $C_{1-4}$ alkoxy, $C_{1-4}$ haloalkoxy, phenoxy, amino, $C_{1-4}$ alkylamino, di-$C_{1-4}$ alkylamino, $C_{1-4}$ alkoxycarbonyl, morpholinocarbonyl and $C_{1-4}$ alkylcarbamoyl groups.

2. A compound according to claim 1 in which n is 0.

3. A compound according to claim 1 wherein $R^1$ and $R^2$ independently represents $C_{2-6}$ alkenyl, $C_{2-6}$ alkynyl, $C_{3-8}$ cycloalkyl or benzyl.

4. A compound according to claim 1 in which n is 0 and each of $R^1$ and $R^2$ independently represents a methyl, ethyl, propyl, hexyl, hydroxyethyl, phenoxyethyl, trifluoromethyl, dibromopropyl, ethoxycarbonylmethyl, diethoxy carbonylmethyl, 2-(ethoxycarbonyl) pentyl, propenyl, propynyl, cyclopentyl, cyclohexyl, methylcarbamoylmethyl, morpholinocarbonylmethyl, benzyl, p-bromobenzyl or tert-butylbenzyl group.

5. A compound according to claim 1 wherein each R represents $C_{1-6}$ alkyl, $C_{1-6}$ haloalkyl, $C_{1-6}$ alkoxy or $C_{1-6}$ haloalkoxy.

6. A process for the preparation of a compound of formula I according to claim 1 which comprises reacting under reaction conditions a compound of formula

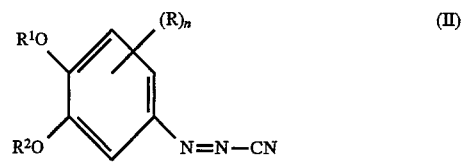

in which n, R, $R^1$ and $R^2$ are as defined in claim 1 with a mixture comprising hydrogen peroxide and at least one of methanoic acid and peroxymethanoic acid.

7. A process for the preparation of a compound of formula I according to claim 6 which comprises reacting with cyanamid under reaction conditions a compound of formula

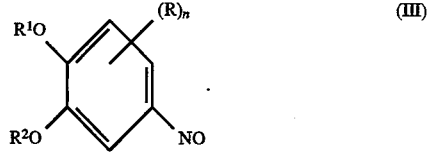

8. A fungicidal composition which comprises a carrier and, as active ingredient, a fungicidally effective amount of a compound of formula I as defined in claim 1.

9. A composition according to claim 8 which comprises at least two carriers, at least one of which is a surface active agent.

10. A method of combating fungus at a locus which comprises treating the locus with a fungicidally effective amount of a compound of formula I as defined in claim 1.

11. A method according to claim 10 in which the locus comprises plants subject to or subjected to fungal attack, seeds of such plants or the medium in which the plants are growing or are to be grown.

12. A method of combating fungus at a locus which comprises treating the locus with a fungicidally effective amount of the composition of claim 8.

13. The method of claim 12 wherein the locus comprises plants subject to or subjected to fungal attack, seeds of such plants or the medium in which the plants are growing or are to be grown.

* * * * *